(12) United States Patent
Utsunomiya

(10) Patent No.: US 7,639,845 B2
(45) Date of Patent: Dec. 29, 2009

(54) DETECTION APPARATUS FOR DETECTING AN AMOUNT OF AN OBJECT OF ANALYSIS IN A FLUID PRESENT IN AN EYE OR ON AN EYE SURFACE

(75) Inventor: Norihiko Utsunomiya, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 501 days.

(21) Appl. No.: 11/194,621

(22) Filed: Aug. 2, 2005

(65) Prior Publication Data

US 2006/0029264 A1 Feb. 9, 2006

(30) Foreign Application Priority Data

Aug. 6, 2004 (JP) ............... 2004-231593

(51) Int. Cl.
*G06K 9/00* (2006.01)
(52) U.S. Cl. .................. 382/117; 382/115; 382/116; 382/118; 382/119
(58) Field of Classification Search ............. 382/117, 382/115, 118; 351/200, 247
See application file for complete search history.

(56) References Cited

U.S. PATENT DOCUMENTS

| 4,014,321 | A | | 3/1977 | March | |
|---|---|---|---|---|---|
| 4,641,349 | A | * | 2/1987 | Flom et al. | 382/117 |
| 6,327,375 | B1 | * | 12/2001 | Matsumoto et al. | 382/117 |
| 6,526,160 | B1 | * | 2/2003 | Ito | 382/117 |
| 6,546,121 | B1 | * | 4/2003 | Oda | 382/117 |
| 7,155,035 | B2 | * | 12/2006 | Kondo et al. | 382/117 |
| 2003/0218719 | A1 | * | 11/2003 | Abourizk et al. | 351/209 |

FOREIGN PATENT DOCUMENTS

| JP | 2000-348116 | 12/2000 |
|---|---|---|
| WO | WO 01/13783 | 3/2001 |

\* cited by examiner

*Primary Examiner*—Brian Q Le
*Assistant Examiner*—Edward Park
(74) *Attorney, Agent, or Firm*—Fitzpatrick, Cella, Harper & Scinto

(57) ABSTRACT

The invention provides a detection apparatus for detecting an amount of an object of analysis in a fluid present in an eye or on an eye surface, including a detector which detects an amount of the object of analysis in the fluid, and a detector which recognizes an iris pattern of the eye.

12 Claims, 15 Drawing Sheets

FIG. 10A

| PRODUCT LOT ID | PRODUCTION DATE | USE LIMIT DATE | LOT CORRECTION DATA |
|---|---|---|---|
| 7H34:8723:23 | 2004/03/28 | 2005/09/30 | −8.234E-3 |
|  |  |  |  |
|  |  |  |  |
|  |  |  |  |
|  |  |  |  |
|  |  |  |  |

FIG. 10B

| PERSONAL ID | IRIS CODE |
|---|---|
| 007G-84AH-22 | 00243F2C3A5A8E9E0A032E5E7A8A9FA05E7E8E2271······ |
|  |  |
|  |  |
|  |  |
|  |  |
|  |  |

FIG. 10C

| PERSONAL ID | INSPECTION DATE | PRODUCT LOT ID | INSPECTION VALUE |
|---|---|---|---|
| 007G-84AH-22 | 2004/08/02 20:34:40 (GMT+0900) | 7H34:8723:23 | 138.2 |
| 007G-84AH-22 | 2004/08/08 19:30:22 (GMT+0900) | 7H34:8723:23 | 140.4 |
| 007G-84AH-22 | 2004/08/10 17:03:03 (GMT+0900) | 7H34:8723:23 | 129.3 |
|  |  |  |  |
|  |  |  |  |
|  |  |  |  |

FIG. 10D

| PERSONAL ID | LOT CORRECTION DATA |
|---|---|
| 007G-84AH-22 | −0.453E-3 |
|  |  |
|  |  |
|  |  |
|  |  |
|  |  |

DETECTION APPARATUS FOR DETECTING AN AMOUNT OF AN OBJECT OF ANALYSIS IN A FLUID PRESENT IN AN EYE OR ON AN EYE SURFACE

BACKGROUND OF THE INVENTION

1. Field of the Invention

The present invention relates to a detection apparatus for detecting an amount of an analysis object in a fluid present in an eye and on an eye surface, and an information management method on an object of analysis.

2. Related Background Art

A technology of non-invasive detection of an object of analysis present in an eye and on an eye surface is disclosed in U.S. Pat. No. 4,014,321, which discloses a technology of positioning a light source and a light-receiving portion across a cornea and detecting a glucose concentration, utilizing a rotation of a polarizing plane by the glucose contained in aqueous humor when the light passes through the cornea.

Also WO01/013783 discloses a technology of utilizing a lens-shaped sensor element in detecting an object of analysis present in an eye and on an eye surface. In this technology, a substance capable of specifically coupling with an object of analysis is fixed to a lens such as a contact lens or an in-eye lens and a concentration of the object of analysis is specified by a competitive reaction with a competing substance containing a fluorescent material.

In such prior technology, there can result a mistake in matching the result of detection of the analysis object in the eye or on the eye surface, with an individual having the eye subjected to the analysis. Furthermore, even in case of a management with an identification code such as an ID number, the individual may be mistaken by an error in an input operation or by an artificial mistake.

On the other hand, a strict management of information on an eye and an individual having such eye is disclosed in Japanese Patent Application Laid-Open No. 2000-348116. This literature discloses a technology of employing a corneal shape analyzing apparatus as optometry means, and of managing ophthalmic data by specifying a subject person subjected to an optometry utilizing an iris recognition. This literature describes that the method disclosed therein allows to avoid a mismatching between the ophthalmic data and the subject person. However, the literature is limited to a management of ophthalmic data utilizing optometry means, and does not include an analysis on the eye fluid.

SUMMARY OF THE INVENTION

The present invention is to provide a detection apparatus capable of strictly correlating a result of detection of an object of analysis in an eye or on an eye surface and a subject person having the eye subjected to the analysis, and a management method on the information relating to the object of analysis.

According to an aspect of the present invention, there is provided a detection apparatus for detecting an amount of an object of analysis in a fluid present in an eye or on an eye surface, comprising:

a detection means which detects an amount of the object of analysis in the fluid; and a means which recognizes an iris pattern of the eye. In the present invention, detecting an amount of an object of analysis in a fluid includes to detect existence or nonexistence of the object of analysis.

The detection means which detects the amount of the object of analysis is preferably a means which detects an optical characteristic.

The means which recognizes the iris pattern of the eye preferably employs an optical means.

The means which recognizes the iris pattern of the eye is preferably formed by a member common with the detection means which detects the amount of the object of analysis. The common member preferably comprises a lens barrel provided with an image pickup device and a lens. Alternatively, the common member preferably comprises a sensor element of a lens shape to be mounted on an eye. A molecule capable of selectively capturing the object of analysis is preferably fixed on a surface of the sensor element.

The detection apparatus preferably further comprises a central processing unit which is connected to a memory unit, a display output apparatus and a communication control unit, and preferably specifies an ID corresponding to a person having the eye, based on an iris pattern recognized by the means which recognizes the iris pattern.

In the detection apparatus, in specifying the ID corresponding to the person the ID is preferably specified by referring to personal iris patterns or data generated from the personal iris patterns, stored in the detection apparatus.

In the detection apparatus, in specifying the ID corresponding to the person the ID is preferably specified by referring to personal iris patterns or data generated from the personal iris patterns, stored in an external computer connected by a network to the detection apparatus.

The detection apparatus preferably has a function of correcting a personal difference in an output value resulting from a combination of the detection apparatus and the person, utilizing personal information corresponding to the specified ID.

The detection apparatus preferably has a function of managing, a detected amount of the object of analysis in correlation with a time data of detection of the amount of the object of analysis for every specified ID.

The detection apparatus preferably further comprises a lens-shaped sensor element to be mounted on the eye, wherein a code to be read is applied to the sensor element. The code applied to the sensor element and the iris pattern are preferably used to specify the ID corresponding to the person having the eye.

The code preferably includes a product number and/or a product lot number of the sensor element.

According to another aspect of the present invention, there is provided an information management method comprising:

a step of acquiring information on an amount of an object of analysis in a fluid present in an eye or on an eye surface;

a step of recognizing an iris pattern of the eye;

a step of identifying a person having the eye based on the pattern recognition; and a step of correlating the information obtained in the information acquiring step with the information obtained in the person identifying step;

wherein the information acquiring step and the pattern recognizing step are executed sequentially using a common image pickup device.

The present invention allows, substantially simultaneously with a measurement of the object of analysis in the fluid present in the eye or on the eye surface, to specify a person who is an object of test. This is particularly important in case the object of analysis is a marker indicating a disease or a health state. Detection methods capable of non-invasive or low-invasive testing are utilized not only in medical therapeutic facilities but also other non-medical facilities. In such other facilities, it is generally not possible to execute a strict correlation between the subject person of test and analytical data of such subject person, but the present invention allows to achieve a strict correlation. Such correlation is essential in consideration of a diagnosis and a therapy executed by a doctor based on the result of test.

Such secure specifying of the tested person means that an error in the amount of the object of analysis, caused by an individual fluctuation, can be corrected at the test, and enables a measurement of a higher precision.

Also in case of executing a quantitative determination of an object of analysis in an eye or on an eye surface with a lens-shaped sensor element, a detection is rendered possible also when the detection of the optical characteristics on a bare eye is difficult for example because of a cataract.

A lens-shaped sensor element also allows, by identifying a code formed on the sensor element, to correct an error in the measured value, resulting from a difference between product types or a fluctuation between product lots, in a similar manner as in the individual fluctuation.

BRIEF DESCRIPTION OF THE DRAWINGS

FIGS. 9A, 9B and 9C are together a flow chart showing an example of a detection and a identification utilizing the detection apparatus of the present invention; and.

FIGS. 10A, 10B, 10C and 10D are schematic views showing examples of data stored in a memory unit applicable to the detection apparatus of the present invention.

DETAILED DESCRIPTION OF THE PREFERRED EMBODIMENTS

A detection apparatus of the present invention is constructed as described above.

In the present invention, a detection means for detecting an amount of an object of analysis can be means which detects an optical characteristic. Also an optical means can be employed for recognizing a pattern of an iris of an eye. Also means which recognizes an iris pattern and detection means which detects an amount of an object of analysis can be constructed with a common member. Such common member may include a lens barrel portion including an image pickup device and a lens. Also there may be employed a sensor element having a shape of a lens to be mounted on an eye in the common member. The detection apparatus may be further provided with a central processing unit connected to a memory unit, a display output apparatus and a communication control unit. It is also possible, based on an iris pattern recognized by the means for recognizing the iris pattern, to specify an ID corresponding to a person having the eye. Also in specifying an ID corresponding to a person, such specifying can be executed by referring to an individual iris pattern or data generated from the iris pattern, stored in the detection apparatus. Also in specifying an ID corresponding to a person, such specifying can be executed by referring to an individual iris pattern or data generated from the iris pattern, stored in an external computer connected by a network to the detection apparatus. It is also possible, utilizing information of a person corresponding to the specified ID, to correct an individual fluctuation in an output value, resulting from a combination of the detection apparatus and the person. It is also possible to manage an amount of the object of analysis in correlation with time data of detection, for each ID specifying the amount of the detected object of analysis. It is furthermore possible to specify an ID indicating a person having the eye, utilizing both a code applied to in the sensor element and an iris pattern. It is furthermore possible to correct a difference in products and/or a difference between lots, utilizing a code which records a product number and/or a product lot number of the sensor element.

In the following, there will be explained an example of the detection apparatus of the present invention, with reference to FIG. 1.

Figure 1:
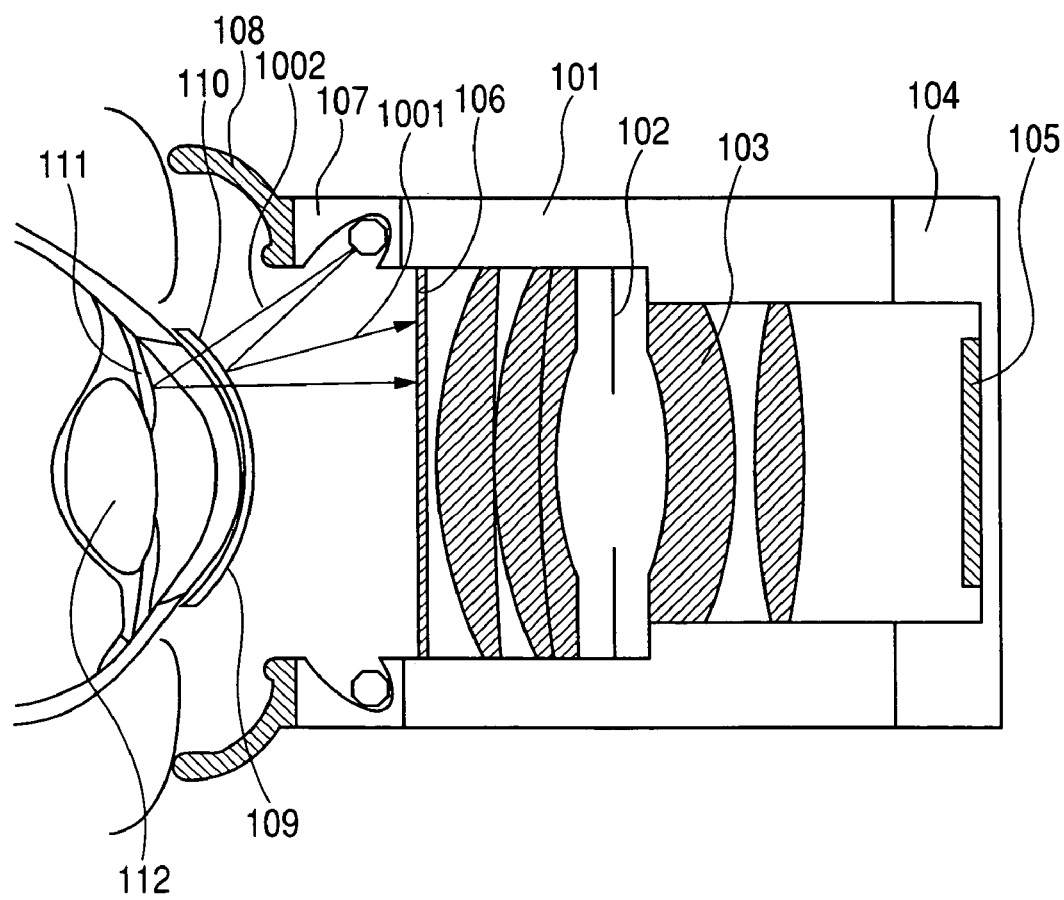
FIG. 1 is a schematic cross-sectional view showing a detecting apparatus of the present invention.
Figure 4:
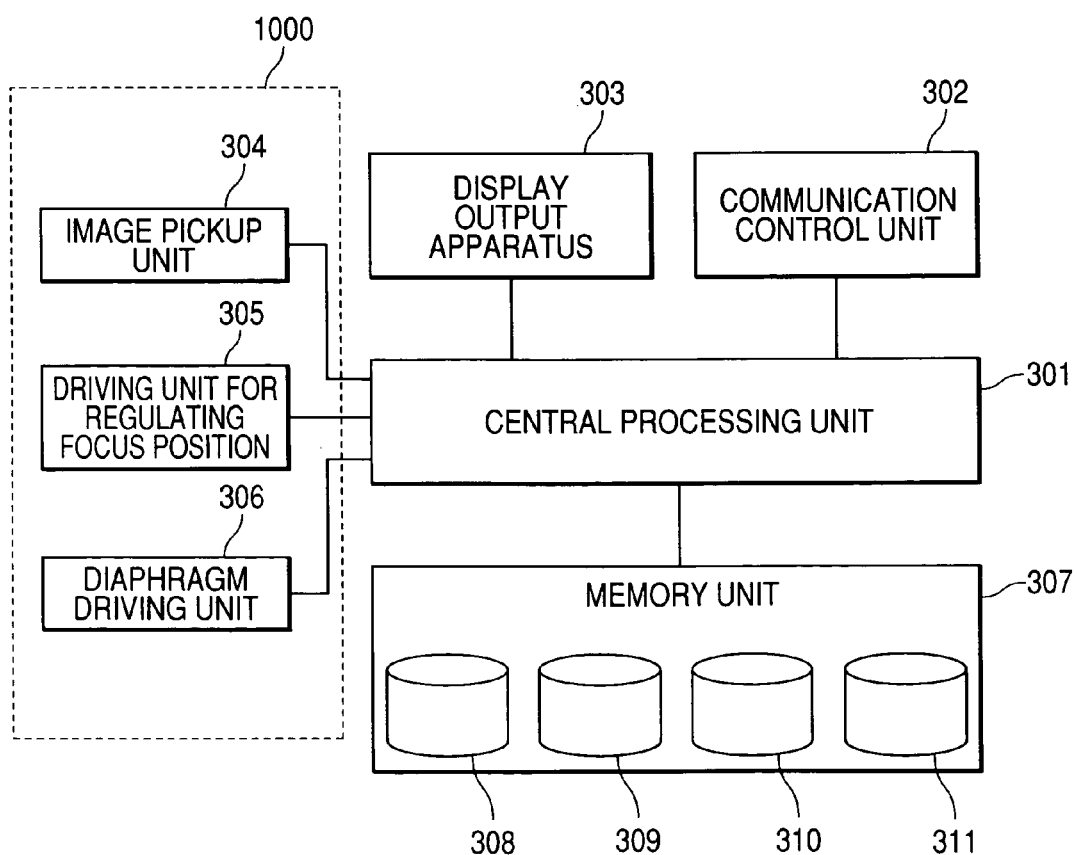
FIG. 4 is a block diagram of a detecting apparatus of the present invention.

FIG. 1 is a schematic cross-sectional view showing an example of the detection apparatus of the present invention. The schematic cross-sectional view shows a portion 1000 in the detection apparatus of the invention shown in FIG. 4. In FIG. 4, there are shown a lens-shaped sensor element 109 mounted on a surface of an eye; an eye lens 112; and an iris pattern 111. There is illustrated a sensor element utilizing a contact lens, but an in-eye lens may also be utilized. In a partial area in the lens-shaped sensor element, there is provided a sensor portion 110 for capturing an object of analysis. A change in the optical characteristics in the sensor portion is observed by the illustrated detection apparatus, whereby an amount of the object of analysis is determined. The sensor portion is preferably provided in a peripheral portion of the lens, in order not to disturb the viewing function of the eye. The detection apparatus shown in FIG. 1 is provided with an optical system including an image pickup device 105, a lens 103, a light source 107 and the like.

Figure 3:
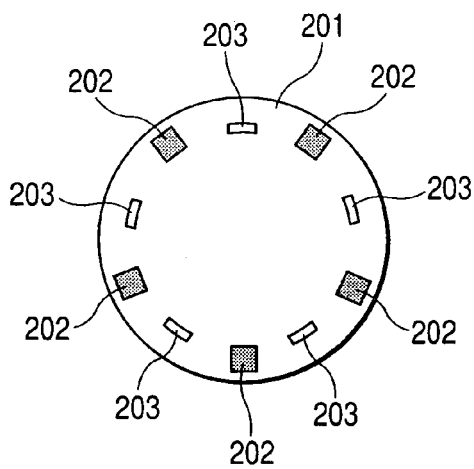
FIG. 3 is a schematic view of a lens-shaped sensor element applicable to the detection apparatus of the present invention.

FIG. 3 is a schematic view of the lens-shaped sensor element 109. In FIG. 3, there are shown a contact lens-shaped sensor element 201, code portions 202, and sensor portions 203. In case the sensor is shaped as a contact lens, the sensor element may be hidden in the shade of an eyelid or eyelashes, and is therefore preferably provided in plural positions in a peripheral portion of the lens.

On a substrate constituting the sensor portion 203, there can be fixed a molecule which selectively captures an object substance. In case the capturing molecules are fixed only on the lens surface, the substrate is not restricted in material and may be formed by a material capable of a covalent bonding with the capturing molecules. However, it is preferable, for the sensor element, to have a larger number of the fixed capturing molecules per unit projected area, so that a porous polymer is preferably employed. Examples of such material include polyethylene glycol hydrogel and Nelfilcon A.

As to the capturing molecule and the object substance of detection, following combinations can be employed. In case the object substance of detection is glucose, concanavalin A is preferably employed as the capturing molecule. Also in case the object substance of detection is a substance having an antigen property such as a protein or a sugar chain, an antibody is preferably employed. Also at the detection in the sensor portion, in case of a combination of glucose and concanavalin A as an object of detection and a capturing molecule, fluorescein dextran, which is a fluorescent dye combining with concanavalin A in competition with glucose, is dropped as an eye-lotion-like reagent onto the lens-shaped sensor element. A competing reaction of glucose in the tear fluid and fluorescein dextran in the reagent indicates in relative manner an amount of fluorescein dextran fixed on the sensor portion. Then an irradiation with an illuminating light of a fluorescence-exciting wavelength of fluorescein dextran is executed, and an amount of fluorescein dextran fixed on the sensor element portion is determined by an amount of fluorescence. An amount of glucose can be obtained by such determination.

The fluid present in the eye or on the eye surface, to be detected by the detection apparatus of the invention, can be tear fluid, aqueous humor or interstitial liquid.

In the foregoing, there has been explained an amount of the object of analysis. Such detection of the amount of the object of analysis also includes detection of presence/absence thereof.

The detection apparatus of the invention is also provided with means which recognizes an iris pattern. An iris pattern 111 of a subject person of test, shown in FIG. 1, can be acquired by utilizing the optical system for observing the change in the optical characteristics.

The configuration of the optical system will be explained in the following with reference to FIG. 1. There are provided a lens barrel 101 for supporting the optical system of the detection apparatus of the invention; a diaphragm mechanism 102 for regulating a light amount entering an image pickup device 105; a lens 103 for focusing images of a sensor portion on the sensor element and of an iris; a casing 104 supporting the image pickup device 105; a protective glass 106 for protecting the imaging lens; and a light source 107 to be used in picking up the images of the sensor portion and the iris. The light source 107 is preferably capable of emitting illuminating lights of plural wavelengths. A specific example of such illuminating lights of plural wavelength is as follows. In case of acquiring an amount of the fluorescence from fluorescein dextran, there is preferred an illuminating light around 495 nm which is the fluorescence exciting wavelength of fluorescein dextran. Also for acquiring the iris pattern, there is preferred an irradiation of a near infrared light. A light source capable of emitting lights of plural wavelengths can be realized by employing a light emitting diode (LED) capable of emitting lights of plural wavelengths and switching the wavelength, or by selecting the wavelength of an illuminating light with unillustrated optical filters.

In FIG. 1, 1001 and 1002 respectively indicate optical paths of the lights emitted from the light source 107 respectively to the sensor element 110 and the iris 111.

There is also provided a light-shielding eye cup 108 for avoiding an external light, in order that the images of the sensor portion and the iris can be picked up only by the illuminating light from the light source 107. Also the imaging lens 103 is so constructed, though not illustrated, as to be capable of moving lens groups to optimum focus positions respectively at the image pickup of the sensor portion 110 and the iris 1111.

EXAMPLES

In the following, the present invention will be explained further with examples, but the present invention is not limited to the following descriptions.

Example 1

A detection apparatus of the present invention in an example 1 will be explained with reference to the accompanying drawings.

FIG. 1 is a cross-sectional view of the detection apparatus of the invention at use. In FIG. 1, there are shown a lens barrel 101 supporting the optical system of the detection apparatus; a diaphragm 102 for regulating a light amount entering an image pickup device 105; an imaging lens 103; a casing 104 for supporting the image pickup device 105; a protective glass 106 for protecting the imaging lens 103; an illuminating light source 107 to be used for image pickup; and a light-shielding eye cup 108 for avoiding an external light. On the side of a tested subject person, there are shown a sensor element 110 of a contact lens shape to be employed in the present detection apparatus; an iris 111 of the tested person; and an eye lens 112.

FIG. 3 is a front view of the sensor element 110. In FIG. 3, there are shown a sensor element 201 of a contact lens shape; and a code portion 202 provided for identifying an individual sensor element, a product type thereof, a user thereof and the like. The code is provided in a two-dimensional QR (quick response) code, but such form is not restrictive. Also this code may be formed by a method detectable with a visible light, or by a method detectable only with an invisible light. Also the illustrated example employs an optically detectable code, but it is also possible to embed a microchip that is identifiable by an electromagnetic wave and to execute an identification by an electromagnetic wave.

There is also provided a sensor portion 203 for detecting an object substance of detection. In FIG. 3, the code portion and the sensor portion are provided in 5 units each in an external peripheral portion of the lens, but the number and the arrangement of such portions are not particularly restricted as long as they are not influenced by the shade of the eyelid and the eyelashes.

FIG. 4 is a block diagram of the detection apparatus of the present example. In FIG. 4, a portion 1000 indicates a detection apparatus shown in FIG. 1. In FIG. 4, there are shown a central processing unit 301 for controlling the entire system; a communication control unit 302 for executing a communication for example with an external computer; a display output apparatus 303 for displaying a detection result or the like; an image pickup unit 304 for executing an image pickup; a driving unit 305 for regulating a focus position; a diaphragm driving unit 306 for regulating a light amount entering the image pickup device; and a memory unit 307 for storing and managing information necessary for the operation of the detection apparatus, including therein product lot data 308, iris code data 309, test history data 310 and individual difference correction data 311. Examples of such data are shown in FIGS. 10A to 10D, in which FIG. 10A shows product lot data indicated by 308 in FIG. 4; FIG. 10B shows iris code data indicated by 309 in FIG. 4; FIG. 10C shows test history data indicated by 310 in FIG. 4; and FIG. 10D shows individual difference correction data indicated by 311 in FIG. 4.

In the following, there will be explained a process flow of the present example. In the present example, the detection process is executed after an eye-lotion-like reagent is dropped onto the lens-shaped sensor element worn by the subject person of test. The eye-lotion-like reagent contains a fluorescent substance, which executes a competing reaction with the object substance of detection captured on the sensor element. An amount fixed on the sensor element varies depending on a concentration of the object substance of detection in the tear fluid on the eye.

Figure 7A:
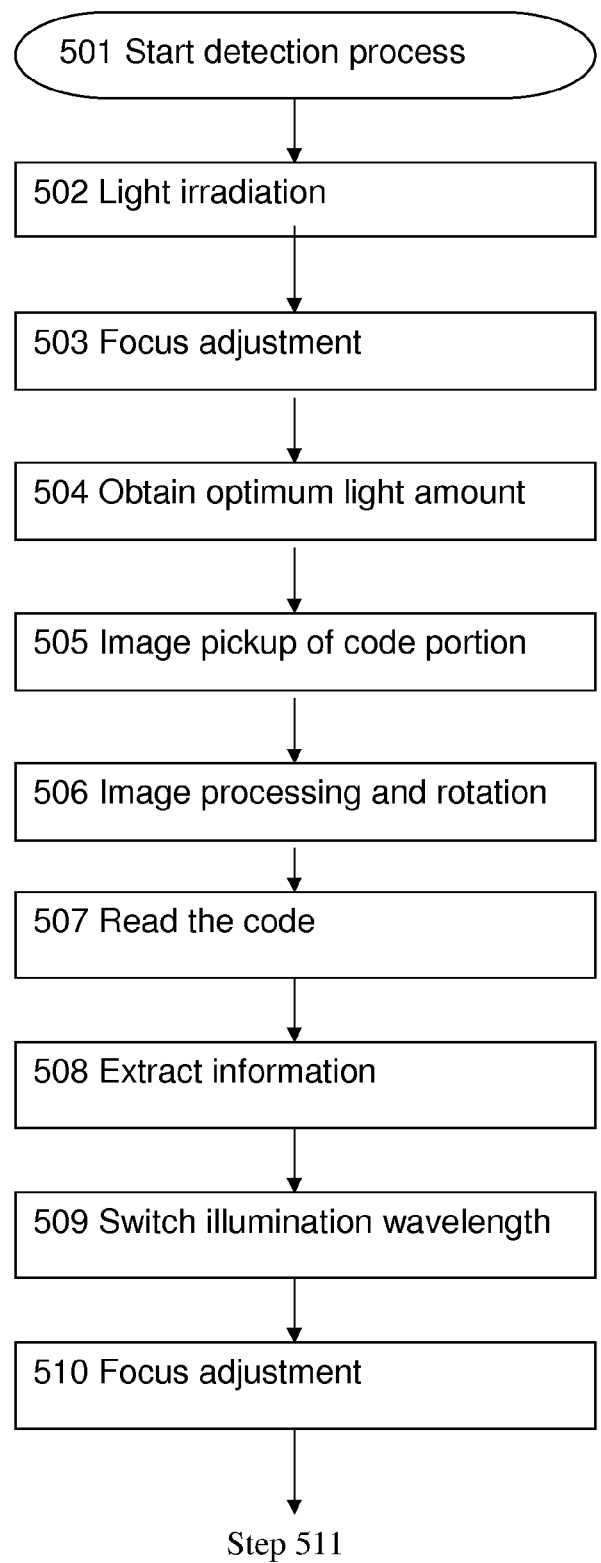
FIGS. 7A, 7B and 7C are together a flow chart showing an example of a detection and a identification utilizing the detection apparatus of the present invention.
Figure 7B:
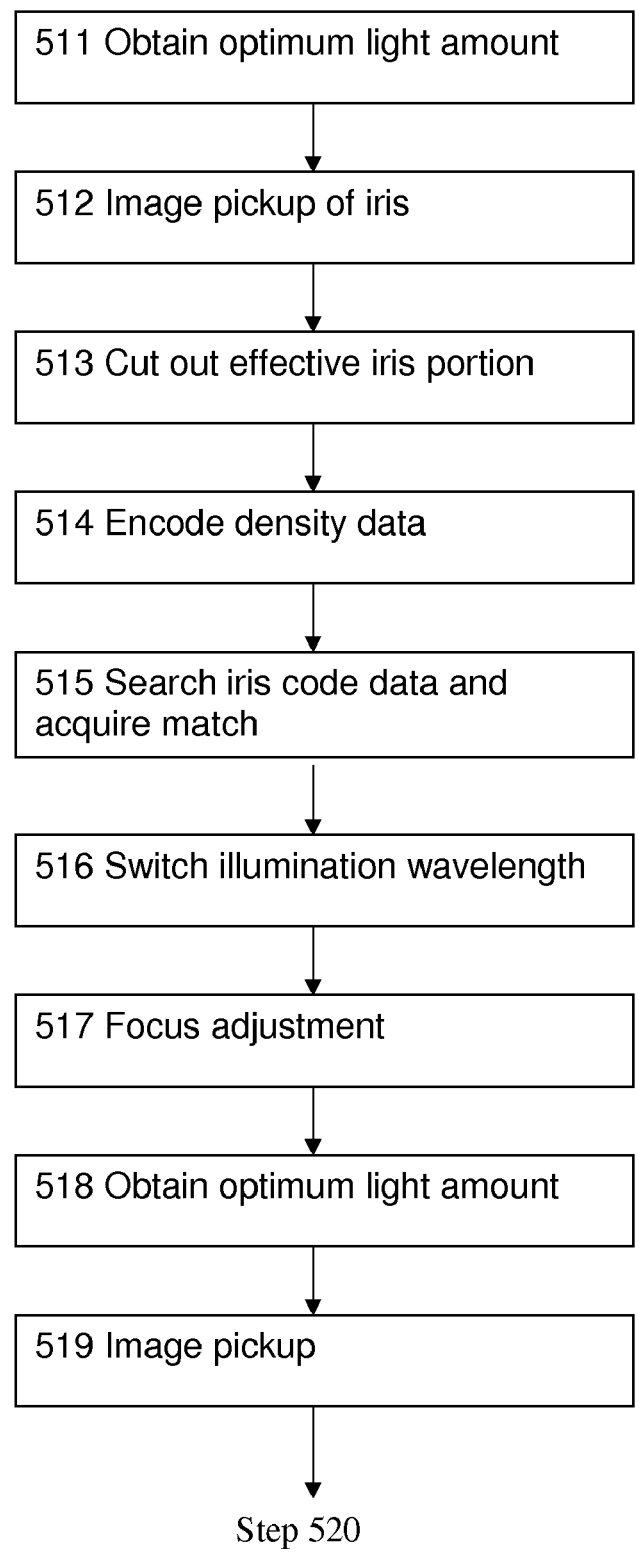
Figure 7C:
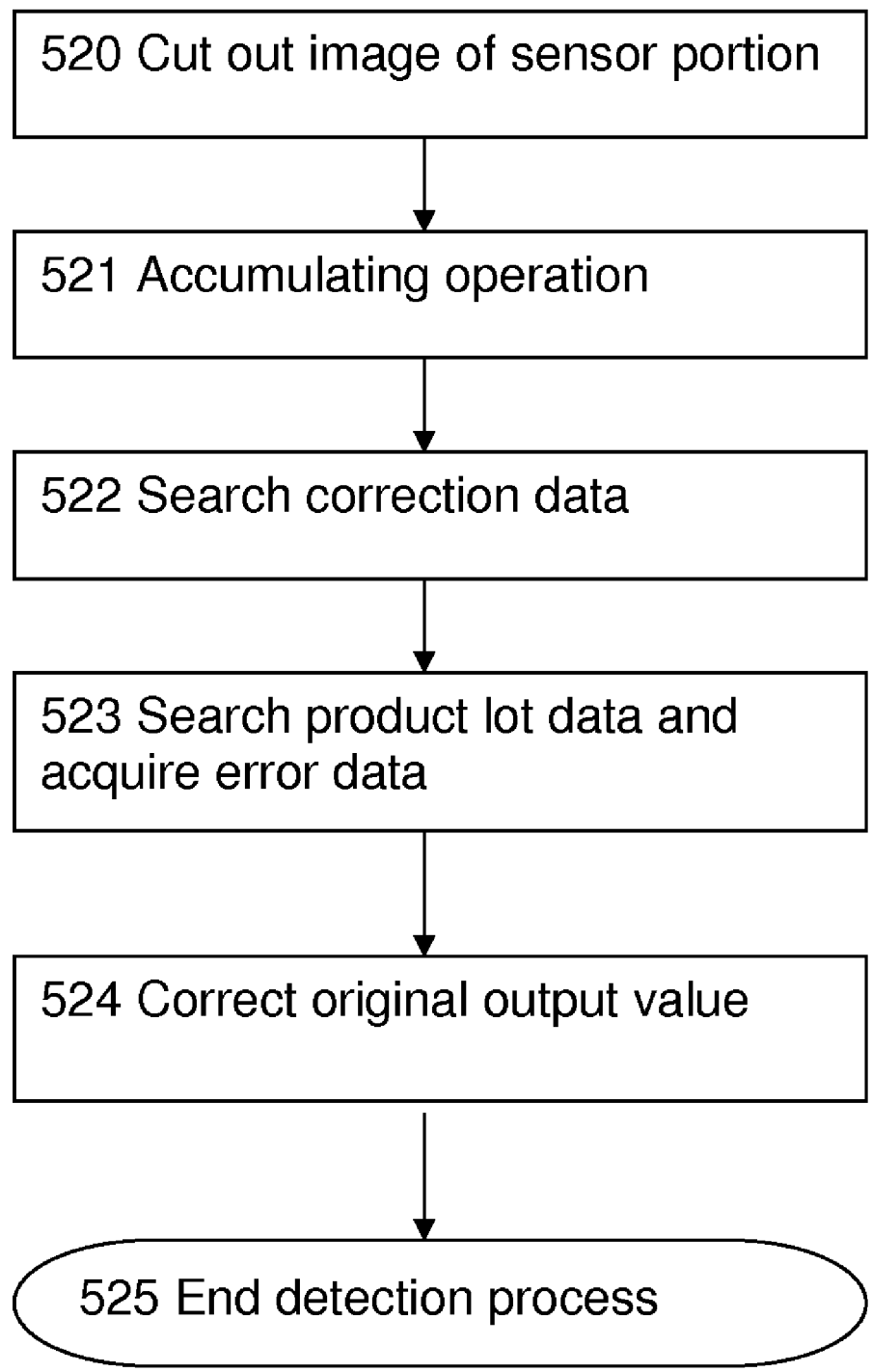

The process flow will be explained in the following with reference to FIGS. 7A-7C.

When an unillustrated detection start button provided on the detection apparatus is depressed, a detection process is started at a step 501.

Then a step 502 executes a light irradiation of a wavelength preferable for an image pickup of the code 202 on the lens, shown in FIG. 3.

Then a step 503 executes a focus adjustment for image pickup of the code on the lens. Such focus adjustment is executed by driving a mechanism 305 shown in FIG. 4. The driving may be executed to a lens position determined in advance, or to an optimum position, depending on a contrast of an output image obtained by the image pickup device 105 shown in FIG. 1.

A step 504 drives the diaphragm 102 shown in FIG. 1, so as to obtain an optimum light amount. Such drive is executed by operating the diaphragm driving unit 306 shown in FIG. 4. As explained above, the drive on diaphragm may be executed to a diaphragm position determined in advance, or to an optimum position, depending on a luminance of an output image of the code portion obtained by the image pickup device 105 shown in FIG. 1.

Then a step 505 executes an actual image pickup of the code portion. In this operation, there are obtained image data picked up by the image pickup device indicated by 105 in FIG. 1 or 304 in FIG. 4.

Then a step 506 executes an image processing to extract a code portion. Then an image rotation process is executed so as to obtain the code portion in an erect state.

Then a step 507 reads the code, based on thus processed image.

From the read code, a personal identification code, a product code and a product lot code contained therein are extracted in step 508.

Then a step 509 switches the illumination to a wavelength suitable for the image pickup of the iris.

Then a step 510 executes a focus adjustment for image pickup of the iris. Such focus adjustment may be executed to a lens position determined in advance, or to an optimum position, depending on a contrast of an output image obtained by the image pickup device 105 shown in FIG. 1.

A step 511 drives the diaphragm so as to obtain an optimum light amount. As explained above, such drive may be executed to a diaphragm position determined in advance, or to an optimum position, depending on a luminance of an output image of the image pickup device 105 shown in FIG. 1.

Then a step 512 executes an image pickup of the iris.

Then a step 513 cuts out an effective iris portion from the obtained data. The effective iris portion means an area positioned between a sclera-cornea boundary and the pupil.

A step 514 encodes density data of thus obtained effective iris portion, utilizing a polar coordinate system having the original point at the center of the iris.

Then a step 515 searches a group of iris code data of one or more persons, stored in advance in the memory 309 of the detection apparatus shown in FIG. 4, utilizing the personal identification code extracted in the step 508, and acquires the iris code data corresponding to the personal identification code. The process is forcedly terminated in case such corresponding iris code data cannot be acquired.

Then a identification process is executed by comparing thus acquired iris code data with the data encoded in the step 514. In case a person is confirmed by the comparison with one of the personal codes obtained in advance, an ID corresponding to such person is used as an ID of the subject person of test. In case a person cannot be identified by the identification of the iris data, the process is forcedly terminated, though such process is not illustrated.

Then a step 516 switches the illumination to a wavelength suitable for the image pickup of the sensor portion.

Then a step 517 executes a focus adjustment for image pickup of the sensor portion. Such focus adjustment may be executed, as explained above, to a position determined in advance, or to an optimum position, depending on an image contrast of the output of the image pickup device.

A step 518 drives the diaphragm 102 shown in FIG. 1, so as to obtain an optimum light amount. A light amount obtained in this step indicates an amount of fluorescence induced from the eye-lotion reagent, excited by the illuminating light in the step 516. Since the amount of the object substance of detection is determined by this light amount, the diaphragm drive in this state is preferably executed, different from the aforementioned diaphragm drive, to a predetermined position.

Then a step 519 executes an image pickup.

Then a step 520 cuts out an image of the sensor portion from the obtained image.

A step 521 executes an accumulating operation of the image of the sensor portion.

A step 522 searches the individual difference correction data 311 shown in FIG. 4, based on the personal ID acquired in the step 515, and acquires correction data for the corresponding personal ID.

A step 523 searches the product lot data 308 shown in FIG. 4, utilizing the product lot code acquired in the step 508, and acquires error data between the products and between the lots. The error data 308 between the products and between the lots, shown in FIG. 4, are to be stored in advance in the detection apparatus. Such data are preferably delivered at the same time when the lens-shaped sensor device is delivered.

Then a step 524 corrects the original output value, based on the personal difference data and the error data among the product lots, acquired in the steps 522, 523.

The detection process is finished at step 525.

In this manner an amount of the object substance of detection can be specified. Thereafter, a detection result is displayed on the display output apparatus 303 shown in FIG. 4. At the same time, the test result is stored in the test history data 310. At such storage, a test date and an ID corresponding to the person are also stored for the purpose of history management of the data. Thus, the amount of the object substances and the acquired iris code data are correlated.

Example 2

Figure 2:
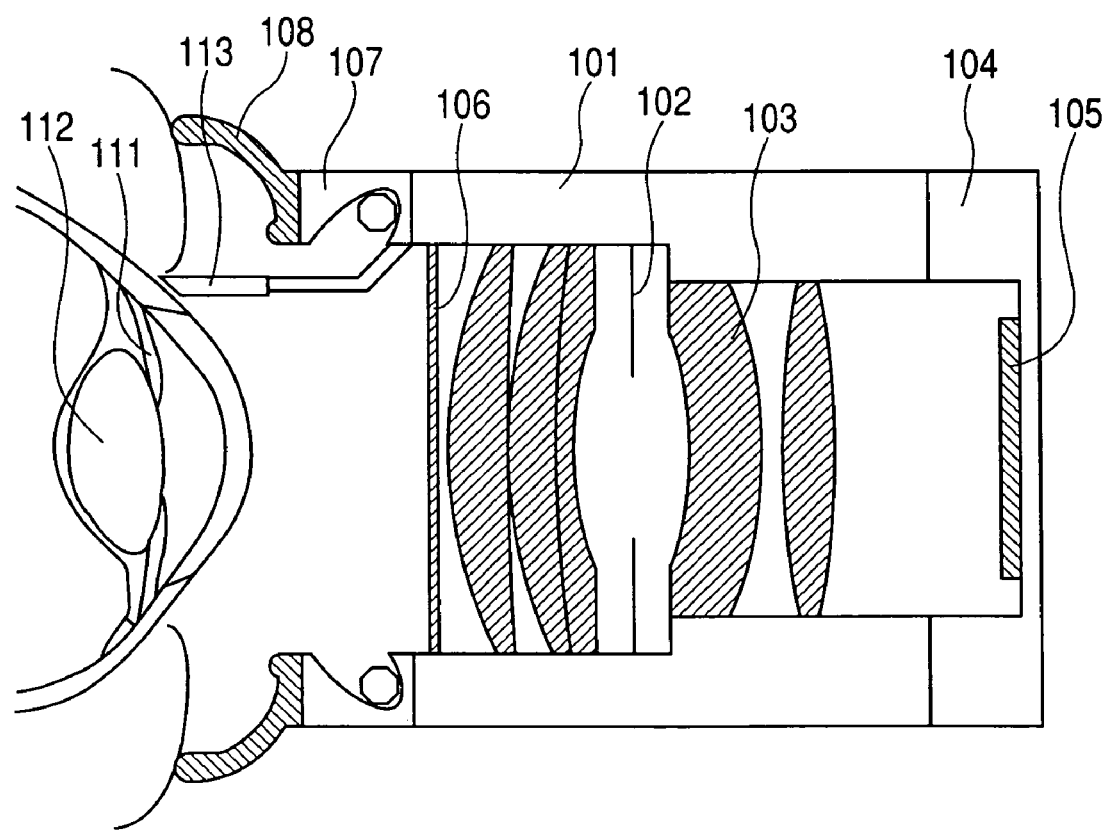
FIG. 2 is a schematic cross-sectional view showing a detecting apparatus of the present invention.

A detection apparatus of the present invention in an example 2 will be explained with reference to FIG. 2. FIG. 2 is a cross-sectional view of the detection apparatus of the present example at use. In FIG. 2, there are shown a lens barrel 101 supporting the optical system of the detection apparatus; a diaphragm 102 for regulating a light amount entering an image pickup device; an imaging lens 103; a casing 104 for supporting an image pickup device 105; a protective glass 106 for protecting the imaging lens 103; an illuminating light source 107 to be used for image pickup; and an electrode probe 113 for detecting an amount of an object substance of detection in tear fluid of a subject person for test. In case the object substance of detection is glucose, the electrode probe is preferably an enzyme electrode utilizing glucose oxidase or glucose dehydrogenase.

There is also provided a light-shielding eye cup 108 for avoiding an external light. On the side of an tested subject person, there are shown an iris 111 of the inspected person; and an eye lens 112.

Figure 5:
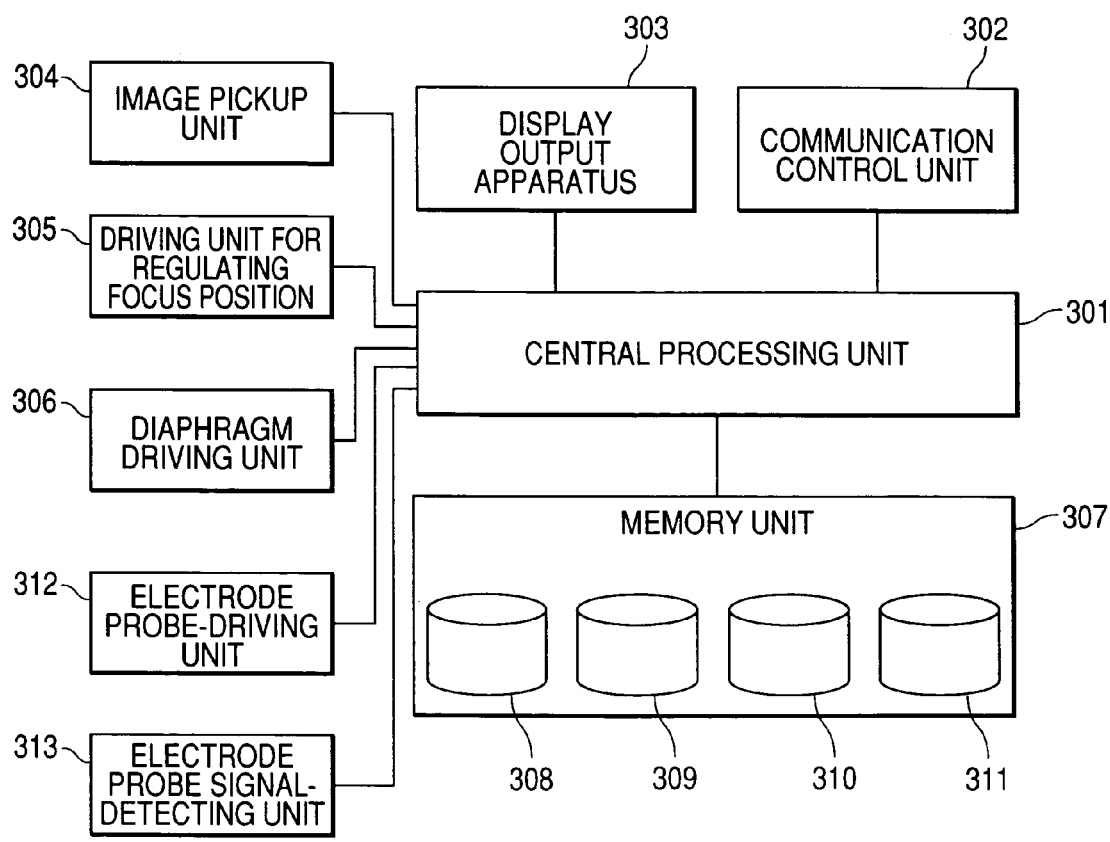
FIG. 5 is a block diagram of a detecting apparatus of the present invention.

FIG. 5 is a block diagram of the detection apparatus of the present example. The block diagram shown in FIG. 5 is same as that shown in FIG. 4, except that a unit 312 for driving the electrode probe and a detection unit 313 for detecting a signal of the electrode probe are attached.

Figure 8A:
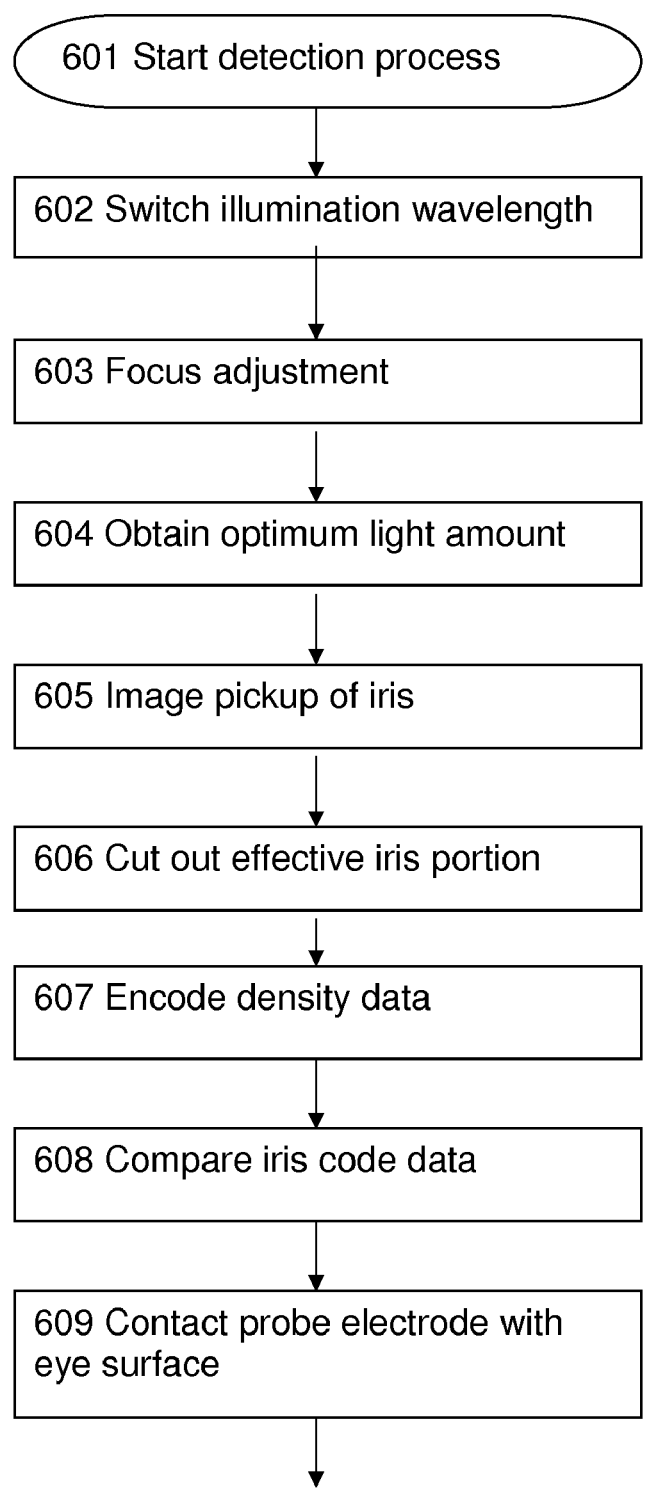
FIGS. 8A and 8B are together a flow chart showing an example of a detection and a identification utilizing the detection apparatus of the present invention.
Figure 8B:
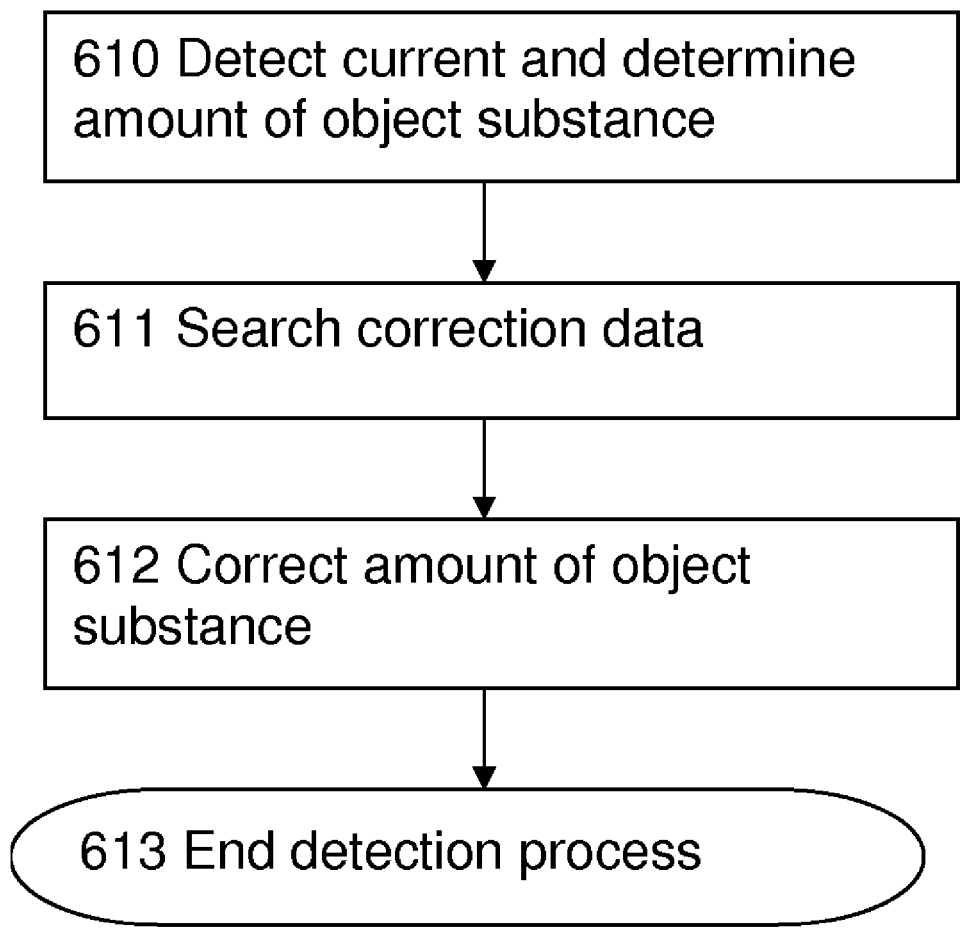

In the following, the process flow will be explained with reference to FIGS. 8A and 8B.

When an unillustrated detection start button provided on the detection apparatus is depressed, a detection process is started at a step 601.

Then a step 602 switches the illumination to a wavelength suitable for iris image pickup.

Then a step 603 executes a focus adjustment for iris image pickup. Such focus adjustment may be executed to a lens position determined in advance, or to an optimum position, depending on a contrast of an output image obtained by the image pickup device 105 shown in FIG. 2.

A step 604 drives the diaphragm so as to obtain an optimum light amount. Such drive, as explained above, may be executed to a diaphragm position determined in advance, or to an optimum position, depending on a luminance of an output image of the image pickup device 105 shown in FIG. 1.

Then a step 605 executes an image pickup of the iris.

Then a step 606 cuts out an effective iris portion from the obtained data. The effective iris portion means an area positioned between a sclera-cornea boundary and the pupil.

A step 607 encodes density data of thus obtained effective iris portion, utilizing a polar coordinate system having the original point at the center of the iris.

Then a step 608 compares a group of iris code data of one or more persons, stored in advance in the memory 309 of the detection apparatus shown in FIG. 5, with the data encoded in the step 607, thereby executing a identification process.

In case a person is confirmed by the comparison with one of the personal codes obtained in advance, an ID corresponding to such person is used as an ID of the subject person of test. In case a person cannot be identified by the identification of the iris data, the process is forcedly terminated. Also instead of forcedly terminating the process, there can also be adopted a process of acquiring the iris data again and executing the identification again.

Then in a step 609, the probe electrode 113 shown in FIG. 2 is contacted with the eye surface of the subject person of test. This operation is executed by giving an instruction to the unit 312 shown in FIG. 5.

Then a step 610 detects a current generated in the probe electrode and determines an amount of the object substance, based on such current.

A step 611 searches the individual difference correction data 311 shown in FIG. 5, based on the personal ID acquired in the step 608.

In step 612, the amount of the object substance determined in the step 610 is corrected based on such correction data.

The detection process is finished at step 613.

In this manner an amount of the object substance of detection can be specified. Thereafter, a detection result is displayed on the display output apparatus 303 shown in FIG. 5. At the same time, the test result is stored in the test history data 310. At such storage, a test date and an ID corresponding to the person are also stored for the purpose of history management of the data.

Example 3

An example 3 shows a case where the detection apparatus of the example 1 is used in a network connection. A detection apparatus has a cross section similar to that of the example 1, as shown in FIG. 1.

Figure 6:
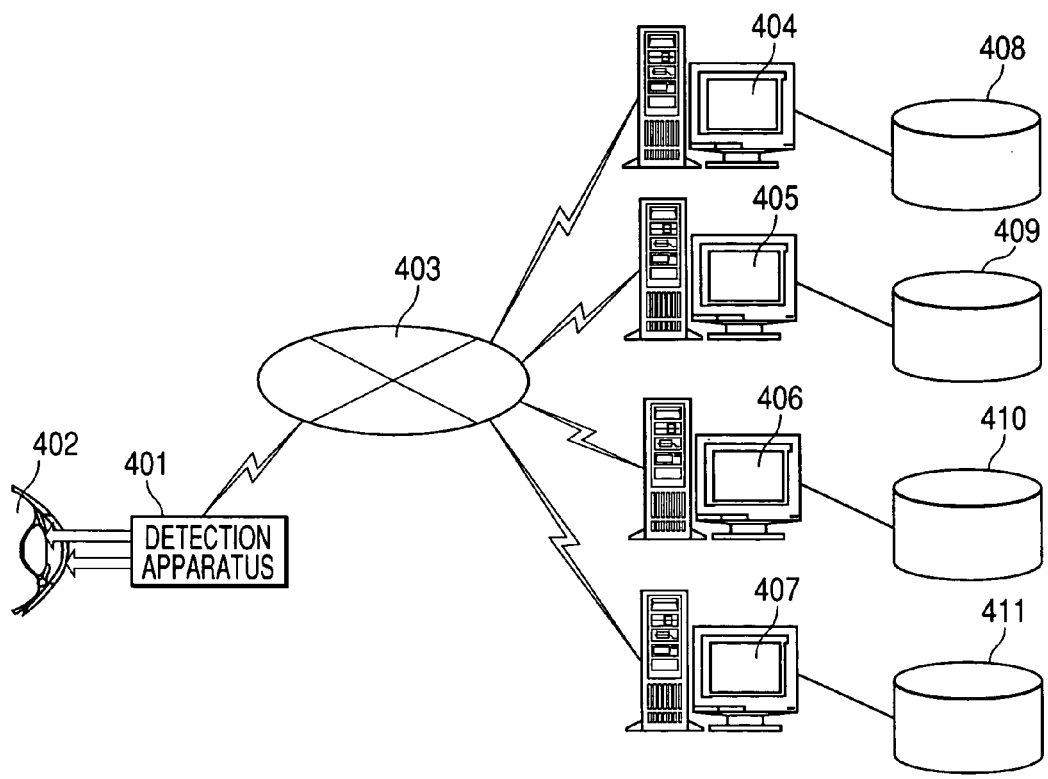
FIG. 6 is a schematic view showing an example of application of the detection apparatus of the present invention.

Also the block diagram of the detection apparatus is same as that shown in FIG. 4. A configuration in case of a network connection is shown in FIG. 6. The configurations shown in FIGS. 1 and 4 will not be repeated as they are already explained in the example 1. In the following, there will be explained the configuration shown in FIG. 6. In FIG. 6, there are shown a detection apparatus 401 employed in the present example; an eyeball 402 of the subject person of test; and a network 403 employed for communication. In FIG. 6, the detection apparatus is directly connected to the network, but it may be connected thereto through a telephone line or the like. There are also provided a management server 404, having a product lot database 408, for managing the error data among the products or the product lots; a identification server 405, having an iris code database 409 managing the encoded individual iris data; a management server 406, having a test data history database 410 for history management of the test data of the detection apparatus for each person; and a server 407, having a individual difference correction database 411 for managing an error of individual fluctuation on the test result. In the following a process flow will be explained. As in the example 1, the subject person of test drops a predetermined amount of an eye-lotion-like reagent onto the lens-shaped sensor.

Figure 9A:
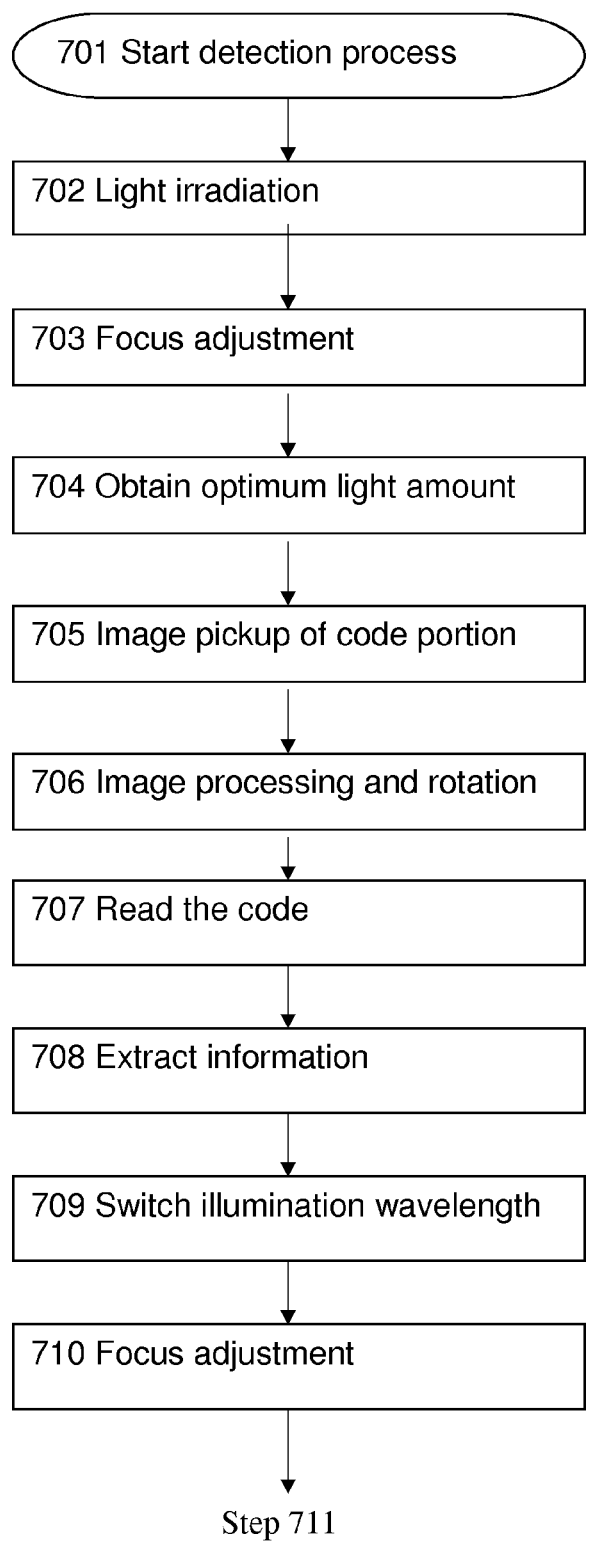
Figure 9B:
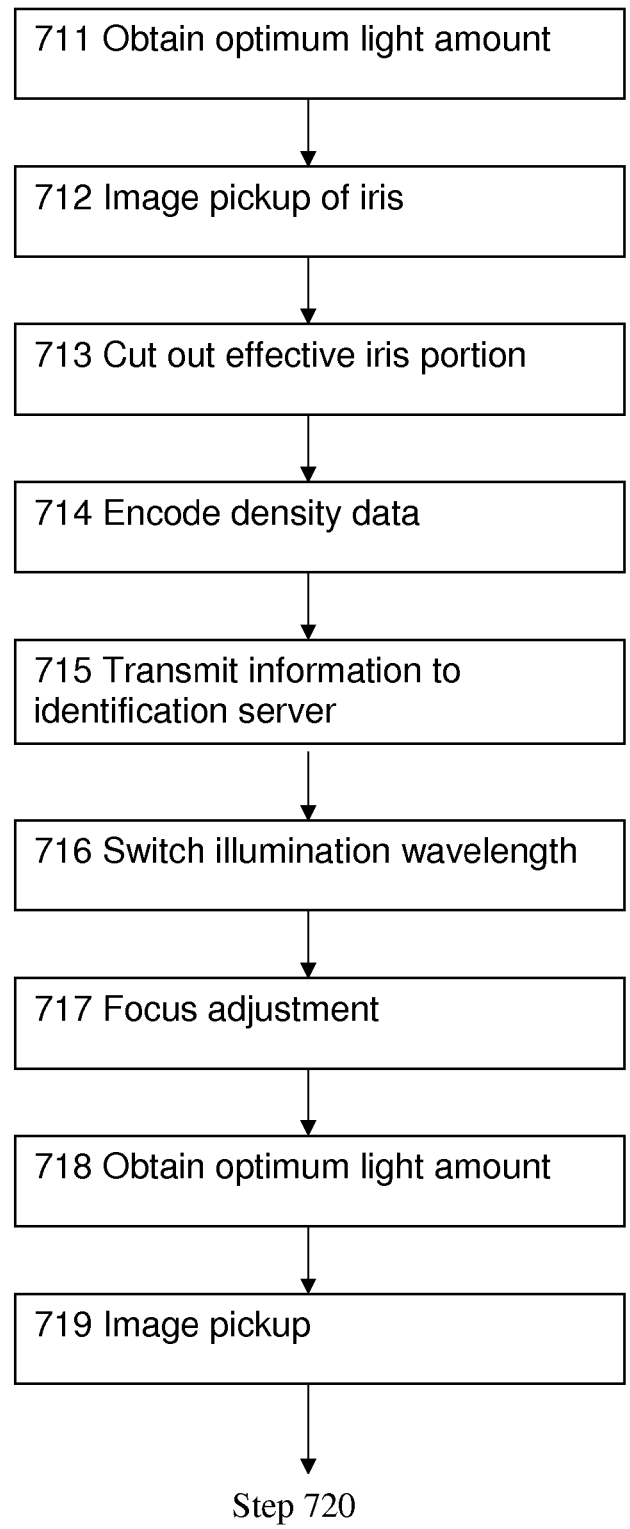
Figure 9C:
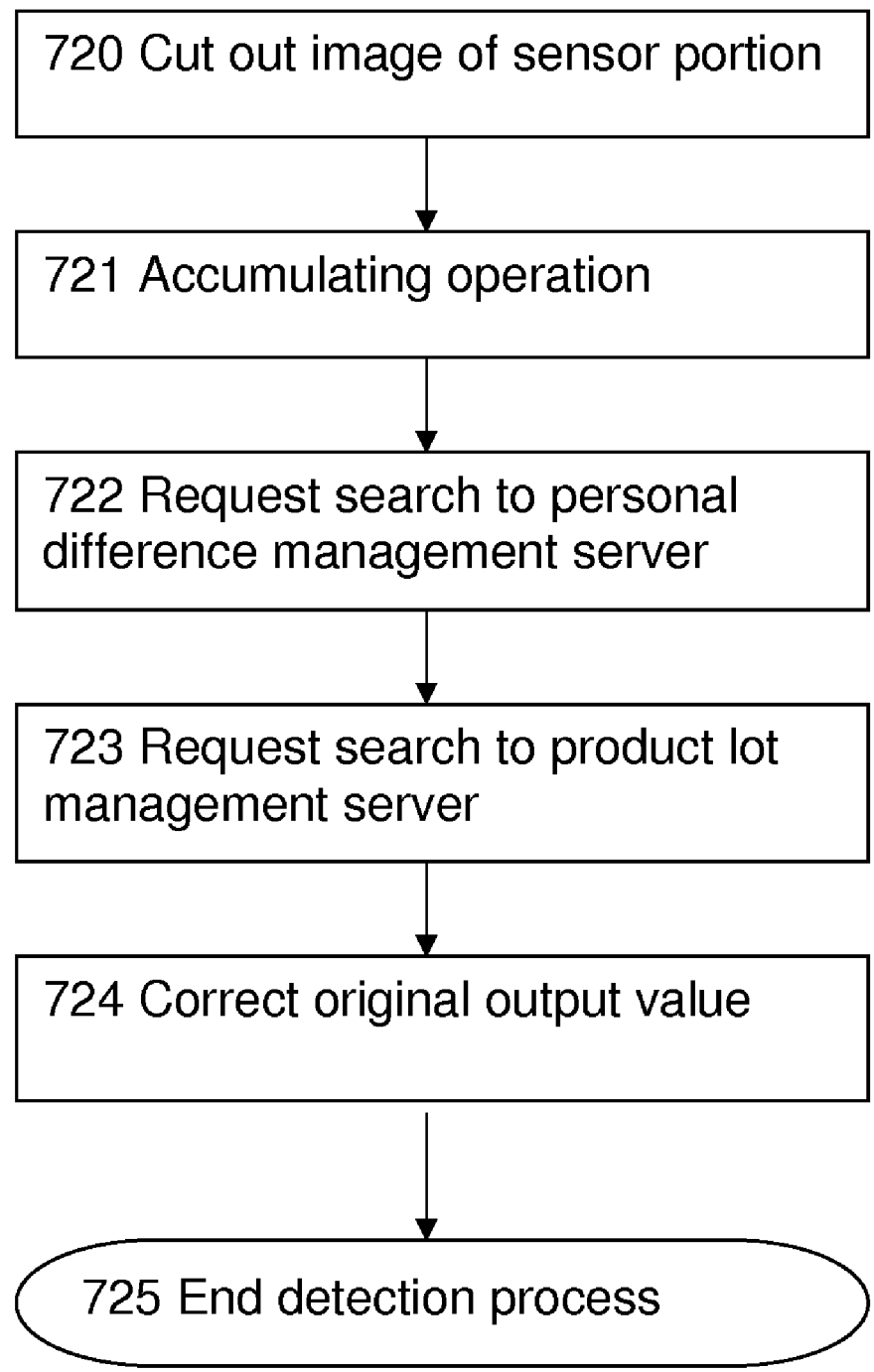

The process flow will be explained with reference to FIGS. 9A-9C.

When an unillustrated detection start button provided on the detection apparatus is depressed, a detection process is started at a step 701.

Then a step 702 executes a light irradiation of a wavelength preferable for an image pickup of the code 202 on the lens, shown in FIG. 3.

Then a step 703 executes a focus adjustment for image pickup of the code on the lens. Such focus adjustment is executed by driving a mechanism 305 shown in FIG. 4. The driving may be executed to a lens position determined in advance, or to an optimum position, depending on a contrast of an output image obtained by the image pickup device 105 shown in FIG. 1.

A step 704 drives the diaphragm 102 shown in FIG. 1, so as to obtain an optimum light amount. Such drive is executed by operating the diaphragm driving unit 306 shown in FIG. 4. As explained above, the drive on diaphragm may be executed to a diaphragm position determined in advance, or to an optimum position, depending on a luminance of an output image of the code portion obtained by the image pickup device 105 shown in FIG. 1.

Then a step 705 executes an actual image pickup of the code in this operation, there are obtained image data picked up by the image pickup device indicated by 105 in FIG. 1 or 304 in FIG. 4.

Then a step 706 executes an image processing to extract a code portion. Then an image rotation process is executed so as to obtain the code portion in an erect state.

Then a step 707 reads the code, based on thus processed image.

From the read code, a personal identification code, a product code and a product lot code contained therein are extracted at step 708.

Then a step 709 switches the illumination to a wavelength suitable for the image pickup of the iris.

Then a step 710 executes a focus adjustment for image pickup of the iris. Such focus adjustment may be executed to a lens position determined in advance, or to an optimum position, depending on a contrast of an output image obtained by the image pickup device 105 shown in FIG. 1.

A step 711 drives the diaphragm so as to obtain an optimum light amount. As explained above, such drive may be executed to a diaphragm position determined in advance, or to an optimum position, depending on aluminance of an output image of the image pickup device 105 shown in FIG. 1.

Then a step 712 executes an image pickup of the iris.

Then a step 713 cuts out an effective iris portion from the obtained data. The effective iris portion means an area positioned between a sclera-cornea boundary and the pupil.

A step 714 encodes density data of thus obtained effective iris portion, utilizing a polar coordinate system having the original point at the center of the iris.

Then a step 715 transmits the encoded iris data obtained in the step 714 and the personal identification code obtained in the step 708, by the communication control unit 202 in FIG. 4, to the identification server 405 on the network as shown in FIG. 6. In this operation, the data are preferably encrypted in order to maintain the secrecy. The identification server, having received the iris data and the personal identification code, searches and acquires the iris data, from the iris code database 409 shown in FIG. 6, by searching with the received personal identification code. The acquired iris data and the received iris data are compared to determine a result of identification, which is returned to the detection apparatus. In case the iris code database does not contain the data of the object person, an unmatching identification result is returns to the detection apparatus.

The detection apparatus which has received the result of identification, in case of a matching identification result, utilizes the personal identification code as an ID of the subject person of test. In case of an unmatching identification result, the process is forcedly terminated, though such process is not illustrated. In the present example, the identification is executed in the identification server, but it may also be executed on the detection apparatus.

Then a step 716 switches the illumination to a wavelength suitable for the image pickup of the sensor portion.

Then a step 717 executes a focus adjustment for image pickup of the sensor portion. Such focus adjustment may be executed, as explained above, to a position determined in advance, or to an optimum position, depending on an image contrast of the output of the image pickup device.

A step 718 drives the diaphragm 102 shown in FIG. 1, so as to obtain an optimum light amount. A light amount obtained in this step indicates an amount of fluorescence induced from the eye-lotion reagent, excited by the illuminating light in the step 716. Since the amount of the object substance of detection is determined by this light amount, the diaphragm drive in this state is preferably executed, different from the aforementioned diaphragm drive, to a predetermined position.

Then a step 719 executes an image pickup.

Then a step 720 cuts out an image of the sensor portion from the obtained image.

A step 721 executes an accumulating operation of the image of the sensor portion.

A step 722 requests a search, based on the personal ID acquired in the step 715, to the personal difference management server 407 shown in FIG. 6, thereby acquiring correction data for the personal difference. The personal difference management server 407 executes the individual difference correction database 411 shown in FIG. 6, and returns individual difference correction data to the detection apparatus.

A step 723 requests a search, based on the product lot code obtained in the step 708, to the product lot management server 404 on the network as shown in FIG. 6. The product lot management server executes a search on the product lot database 408 shown in FIG. 6, and acquires and returns error data for the product and the lost to the detection apparatus.

The aforementioned product lot database is preferably renewed by the manufacturer or the sales company of the lens-shaped sensor element.

Then a step 724 corrects the original output value, based on the personal difference data and the error data among the product lots, acquired in the steps 722, 723.

The detection process is finished at step 725.

In this manner an amount of the object substance of detection can be specified. Thereafter, a detection result is displayed on the display output apparatus 303 shown in FIG. 4. At the same time, an test date, an ID corresponding to the person and the test result are transmitted to the test history management server 406 in FIG. 6 on the network, which stores the personal ID, the test date and the test result thus received in the test history database.

This application claims priority from Japanese Patent Application No. 2004-231593 filed on Aug. 6, 2004, which is hereby incorporated by reference herein.

What is claimed is:

1. An apparatus for detecting an amount of an object of analysis by using a sensor element, the sensor element of a contact lens shape on an eye, comprising:
   a lens barrel which comprises:
      a light source for illuminating the sensor element,
      an image pickup device for picking up an image of an iris, and
      a light-shielding member for preventing external light from entering inside of the lens barrel;
   wherein the sensor element includes
      a sensor portion comprised of a substrate for fixing a molecule capable of selectively capturing the object of analysis and
      a code portion for identifying a subject person; and
   wherein (i) an image of the code portion is picked up by the image pickup device, illuminating the code portion with the light source, (ii) an image of an iris is picked up by the image pickup device, illuminating the eye with the light source (iii) and the image of the code portion and the image of the iris are compared to each other to identify the subject person;
   wherein, with a reagent comprised of a fluorescent substance present on said sensor element, the fluorescent substance executing a competing reaction with the object of analysis, and the light source illuminating said sensor element, the amount of the object of analysis captured by the capturing molecule is detected by an amount of fluorescence of the fluorescent substance, and
   wherein the sensor portion is irradiated with light having a wavelength different from the wavelength of light with which the code portion and the iris are irradiated to detect the amount of the object of analysis when the subject person is identified from a sensor portion for identifying.

2. A detection apparatus according to claim 1, further comprising a memory unit for storing the encoded data, wherein the ID corresponding to the person having the iris is specified by referring to the encoded data or data generated from the encoded data stored in the memory unit.

3. A detection apparatus according to claim 1, wherein, in specifying the ID corresponding to the person, the ID is specified by referring to personal iris patterns or data generated from the personal iris patterns, stored in an external computer connected by a network to the detection apparatus.

4. A detection apparatus according to claim 1, having a function of correcting a personal difference in an output value resulting from a combination of the detection apparatus and the person, utilizing personal information corresponding to the specified ID.

5. A detection apparatus according to claim 1, having a function of managing a detected amount of the object of analysis in correlation with a time data of detection of the amount of the object of analysis for every specified ID.

6. A detection apparatus according to claim 1, wherein a code to be read is applied to said sensor element.

7. A detection apparatus according to claim 6, wherein the code applied to said sensor element and an iris pattern are used to specify the ID corresponding to the person having the iris.

8. A detection apparatus according to claim 6, wherein the code includes at least one of a product number and a product lot number of said sensor element.

9. A detection apparatus according to claim 1, wherein the substrate is capable of covalent bonding with the capturing molecule.

10. A detection apparatus according to claim 1, wherein the sensor portion is provided in a peripheral portion of said sensor element.

11. A detection apparatus according to claim 1, wherein said lens barrel is provided with an image pickup device for picking up an image of an iris, an effective iris portion is cut out from data obtained by picking up the image of the iris, and density data of the effective iris portion is encoded utilizing a polar coordinate system having an origin at the center of the iris, whereby a person having the iris can be identified based on the coded density data.

12. The apparatus according to claim 1, further comprising:

a dropping portion for dropping a reagent comprised of a fluorescent substance which executes a competing reaction with the object of analysis onto the sensor element, a light amount-acquiring portion for acquiring a light amount of the fluorescent substance excited by illuminating the sensor element with the light source, and a detecting portion for detecting by the light amount the amount of the object of analysis captured by the molecule.

* * * * *